United States Patent
Burney et al.

(10) Patent No.: US 6,447,477 B2
(45) Date of Patent: *Sep. 10, 2002

(54) SURGICAL AND PHARMACEUTICAL SITE ACCESS GUIDE AND METHODS

(75) Inventors: Bryan T. Burney, Fishers; David L. Schroeder, Franklin; Michael E. Miller, Trafalgar, all of IN (US)

(73) Assignee: EMX, Inc., Franklin, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/765,732

(22) Filed: Jan. 11, 2001

Related U.S. Application Data (63) Continuation of application No. 09/117,755, filed as application No. PCT/US97/02103 on Feb. 10, 1997, now Pat. No. 6,203,524, which is a continuation-in-part of application No. 08/599,381, filed on Feb. 9, 1996, now Pat. No. 5,800,389.

(51) Int. Cl.[7] .............................................. A61M 11/00
(52) U.S. Cl. ............................. 604/93.01; 604/164.01; 604/264; 604/158; 604/159
(58) Field of Search ....................... 604/93.01, 164.01, 604/164.04, 264, 158, 159, 162, 163

(56) References Cited

U.S. PATENT DOCUMENTS

| | | |
|---|---|---|
| 1,867,624 A | 7/1932 | Hoffman |
| 3,001,522 A | 9/1961 | Silverman |
| 4,517,965 A | 5/1985 | Ellison |
| 4,552,554 A | 11/1985 | Gould et al. |
| 4,573,975 A | 3/1986 | Frist et al. |
| 4,632,668 A | 12/1986 | Wilson, Jr. et al. |
| D297,365 S | 8/1988 | Barnett |
| 4,842,585 A | 6/1989 | Witt |
| 4,900,309 A | 2/1990 | Netherton et al. |
| 5,030,212 A | 7/1991 | Rose |
| 5,067,944 A | 11/1991 | Nichols |
| 5,069,669 A | 12/1991 | Kole |
| 5,147,308 A | 9/1992 | Singer |
| 5,147,314 A | 9/1992 | Vaillancourt |
| 5,163,915 A | 11/1992 | Holleron |
| 5,167,643 A | 12/1992 | Lynn |
| 5,180,374 A | 1/1993 | Porteous |
| 5,224,488 A | 7/1993 | Neuffer |
| 5,242,448 A | 9/1993 | Pettine et al. |
| 5,301,684 A | 4/1994 | Ogirala |
| 5,304,148 A | 4/1994 | Lannoye et al. |
| 5,360,416 A | 11/1994 | Ausherman et al. |
| 5,366,490 A | 11/1994 | Edwards et al. |
| 5,425,376 A | 6/1995 | Banys et al. |
| 5,514,111 A | 5/1996 | Phelps |

OTHER PUBLICATIONS

Grimm, Peter D. et al., "Ultrasound–Guided Transperineal Implantation of Iodine 125 and Palladium–103 for the Treatment of Early–Stage Prostate Cancer", New Techniques in Prostate Surgery, vol. 2, No. 7, Oct. 1994, pp. 113–126.

(List continued on next page.)

Primary Examiner—Dinh X. Nguyen
(74) Attorney, Agent, or Firm—Leagre Chandler & Millard LLP (57) ABSTRACT

A guide (100) is provided for biopsy and microtherapy which includes an introducer cannula (120) defining a lumen (125) sized to receive a diagnostic or therapeutic item therethrough and a lateral opening (124) in communication with the lumen (125) adjacent the first end (121) of the cannula (120). The invention also includes a solid tip (130) having an anatomically distal end (131) secured to the first end (121) of the cannula (120) and a proximal end (132) configured to pierce tissue. A ramp (135) is disposed within the cannula (120) at an end (136) of the lateral opening (124) adjacent the first end (121) of the cannula (120). The ramp (135) is inclined toward the lateral opening (124), whereby the item will be deflected through the lateral opening (124) as it advances within the lumen (125) and exits the cannula (120). In some embodiments, the item is a biopsy needle, ablation means or a radiopharmaceutical seed. The invention also includes methods of obtaining a biopsy sample and methods for treating lesions.

14 Claims, 5 Drawing Sheets

OTHER PUBLICATIONS

Gronemeyer, Dietrich, M.D. et al., "Image–Guided Access Enhances Microtherapy", Interactive Guidance, Nov. 1996, pp. IR2–IR5.

Hou, Ming–Feng, MD et al., "A Simple Method of Duct Cannulation and Localization for Galactography before Excision in Patients with Nipple Discharge", Radiology May 1995, pp. 568–569.

Karstrup, Steen et al. "Nonsurgical Treatement of Primary Hyperparathyroidism with Sonographically Guided Percutaneous Injection of Ethanol: Results in a SElected Series of Patients", Herlev Hospital, University of Copenhagen, DK, pp. 1087–1090.

Karstrup, Steen et al. "Ultrasonically Guided Fine Needle Aspiration of Suggested Enlarged Parathyroid Glands", Herlev Hospital, University of Copenhagen, DK, pp. 213–216.

Tabar, Lazlo, MD et al., "Galactography: The Diagnostic Procedure of Choice for Nipple Discharge" Radiology, vol. 149 No. 1, Oct. 1983, pp. 31–38.

Solbiati, Luigi, MD et al. "Percutaneous Ethanol Injection of Parathyroid Tumors Under US Guidance: Treatment for Secondary Hyperparathyroidism", Radiology, vol. 155, No. 3, Jun. 1985, pp. 607–610.

Hurley, Ronald "Minimizing Postdural Puncture Headache".

"ELDOR Needle Minipack" Alexander Medical, Inc. Coral Springs, Florida.

SURGICAL AND PHARMACEUTICAL SITE ACCESS GUIDE AND METHODS

This application is a continuation of application Ser. No. 09/117,755, filed Aug. 4, 1998, now U.S. Pat. No. 6,203,524 nationalized from PCT Application No. 97/02103, filed Feb. 10, 1997, which is a continuation-in-part of Ser. No. 08/599,381, filed Feb. 9, 1996, now U.S. Pat. No. 5,800,389.

FIELD OF THE INVENTION

The present invention broadly concerns surgical and pharmaceutical delivery systems. More specifically, the invention concerns biopsy devices which provide safe and efficient coaxial, cofocal and eccentric sampling or delivery with only a single guide device placement.

BACKGROUND OF THE INVENTION

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

During the biopsy procedure, care is taken to minimize the physical trauma inflicted upon the intervening tissues that surround the affected area or target tissue and at the same time to protect the practitioner from health hazards. One typical biopsy procedure includes inserting a hollow biopsy needle through the intervening tissue into the target tissue to be sampled. The sample tissue is then harvested through the needle by applying suction through the needle, typically with a syringe.

Other more complicated devices have been developed in an attempt to improve biopsy procedures and results. Three references, U.S. Pat. No. 5,301,684 to Ogirala; U.S. Pat. No. 5,425,376 to Banys et al.; and U.S. Pat. No. 5,224,488 to Neuffer disclose biopsy devices employing lateral openings. The Ogirala reference shows a cutting edge on a spring operated flap over the lateral opening. The Neuffer device includes a twisted flexible cutting strip contained within the needle. Turning a handle flexes the strip through the lateral opening. The surgeon then rotates the device to cut a sample and guide it into the needle. The Banys patent discloses a biopsy needle attached to a syringe having a cannula which is slidable over the needle to alternately expose or cover the lateral opening. Both the cannula and the lateral opening provide a tissue cutting edge. Using the Banys device, the surgeon is required to maneuver the needle so that the sample is placed within the needle and the slide the cannula to cover the lateral opening and trap the sample within the needle.

Another reference of interest, U.S. Pat. No. 3,001,522 to Silverman, discloses a biopsy device having a pair of resilient arms which extend from the end of the device. The arms are disposed at an angle away from the axis of the device and are oppositely beveled to urge the arms apart as they are inserted into tissue. The Silverman device does not include a side port or a ramp for exit of a biopsy needle from an introducer device.

The prior art biopsy procedures and devices suffer from several disadvantages. First, they do not adequately address the need for multiple samplings. It is often desirable to sample the tissue surrounding a lesion in addition to the lesion itself. Also, needle aspiration biopsies are prone to sampling errors, which necessitate reinsertions of the biopsy needle. Furthermore, none of the known prior devices accommodate the need to reach behind vital organs and structures because they require a straight path to the target. Current systems require multiple device insertions to sample tissue eccentric to the initial needle placement. Unfortunately, multiple insertions of the biopsy device increase patient discomfort, surgical time and the risk of complications.

Another important consideration in biopsy needle design is that the amount of tissue harvested be sufficient for the types of analysis to be done. Although major improvements have been made in the sensitivity of test procedures and apparatus so that smaller samples have become sufficient for each test, the number of different test procedures and the importance of having the capability for redundant or confirming testing still necessitates having a suitable sample size. However, the size of the tissue sample is limited by the size of the opening in the sampling end of known biopsy needles. Where the size of the tissue collected is inadequate, multiple device insertions will be required. This is often complicated by the difficulty in returning to the exact location required as well as the increased trauma to the patient.

Current systems are also limited in that they cause unnecessary trauma to the patient. For example, lesions located behind important vascular structures are difficult to reach without causing damage. Also, pushing a hollow needle through intervening tissues to the target area results in the accumulation of unwanted tissue in the needle, which can interfere with or complicate sample analysis. Finally, the open end of a biopsy needle or the projecting edge of a cutting cannula can tear the surrounding tissue unnecessarily, increasing trauma to the patient.

Current systems which attempt to address some of these concerns are generally complicated spring-operated or multi-component devices. Furthermore, these devices require multiple insertions for sampling eccentric to the initial device placement. Accordingly, a need has remained for biopsy devices which compensate for sampling errors and accommodate the need for safely and efficiently obtaining multiple samples with a single device placement.

Once pathology is diagnosed, the site must be accessed for treatment. Conventionally, malignancies are treated indirectly by chemotherapy and/or radiation or directly by removal of the lesion. Each of these approaches has limitations and undesirable side effects. Surgery carries risks of infections and adverse anesthesia effects and does not always improve the outcome. Surgery may not be an option due to patient condition or the location and size of the tumor. Furthermore, some studies have suggested that surgery may be associated with the spread of some cancers. Chemotherapy and radiotherapy affect both normal and malignant dividing cells, leading to, for example, hair loss, nausea and decreases in all blood cell types. In spite of the emotional and physical costs paid, conventional treatments do not always increase length of survival or quality of life of patients.

Percutaneous procedures are now favored for their reduced risks and trauma. Ideally, conditions would be treated locally through a single port instead of systematically. Such treatments would be more precise as well as less traumatic and invasive. Various conditions have been treated percutaneously with some success using such methods as mechanical, chemical and radio-ablation. One limitation of these known procedures is the accuracy of needle placement.

Transperineal radioactive seed implantation shows great promise for treating prostate cancer (Grimm et al., New Techs in Pros. Surg. 2:113–126, 1994). This percutaneous, outpatient treatment provides more precise and effective dosing than open approaches with lower morbidity than external beam radiation. While this procedure represents a major advance in treating prostate cancer, improvements are still needed in obtaining reproducible and accurate needle placements. The methods involve multiple needle placements and removal. A depth reference point must be calculated by measuring the distance from the hub of the needle for each placement. It is important that the needle and seed placement be precise. Needle placements of more than 1–2 mm off the targeted coordinate must be repositioned. Needle placements which are otherwise on target must be repositioned if the needle insertion causes lateral rotation of the prostate. This procedure also requires at least two surgeons for manipulation of the needles and stylets to prevent improper deboarding of the pellets.

Percutaneous fine-needle alcohol ablation has also been used with some success in the treatment of tumors. Karstrup et al. (AJR: 154: 1087–1090, 1990) disclose ablation of parathyroid tumors under ultrasonographic guidance. Precise needle placement is essential due to the important neurological and vascular structures in the area. The authors recommend small amounts of alcohol and precise placement of the needle tip to avoid nerve damage.

Accordingly, there is a need for less invasive and traumatic and yet more precise and localized treatments of lesions.

SUMMARY OF THE INVENTION

Briefly describing one aspect of the invention, there is provided a surgical and pharmaceutical site access guide device which allows coaxial, cofocal and eccentric sampling and delivery with a single device placement. The invention includes an introducer device that includes a cannula having a first end and a second end and defining a lumen. The second end of the cannula defines an aperture. The cannula defines a lateral opening in communication with the lumen adjacent the first end.

The introducer devices also include a solid tip having an anatomically distal end secured to the first end of the cannula and a proximal end configured to pierce tissue. In one aspect of the invention, a ramp is disposed within the cannula at an end of the lateral opening adjacent the first end of the cannula. The ramp is inclined toward the lateral opening whereby the items will be deflected through the lateral opening as they are advance within the lumen and exit the cannula.

In one specific aspect of the invention an introducer also includes a hub attached to the second end of the cannula which includes a gripping portion configured to be held when inserting and positioning the introducer. The hub defines a channel which is in communication with the aperture.

In one aspect of the invention, the introducer includes means for protecting the practitioner from inadvertent needle sticks. In a specific embodiment of the invention, the means includes a flange that projects from the hub at a location anatomically distal from the gripping portion. The flange is configured to prevent inadvertent needle sticks when a biopsy needle is inserted into the introducer.

In one specific embodiment, a biopsy needle having a bend adjacent an anatomically proximal end of the needle is provided. The bend deflects the proximal end of the needle at an angle away from the longitudinal axis of the needle.

The invention also includes methods for obtaining a biopsy sample and methods of making a guide device. According to procedures for obtaining a biopsy sample of this invention, a biopsy needle introducer of this invention is inserted into a patient at the biopsy site. The biopsy needle is then inserted into the lumen of the introducer and advanced until the proximal end of the biopsy needle projects through the lateral opening at an angle relative to the introducer and into the biopsy sample site.

In one aspect of the invention, the biopsy needle is withdrawn from the sample site and the introducer rotated. The biopsy needle is then reinserted into the introducer and advanced to obtain a second biopsy sample from a location eccentric from the first biopsy sample site.

In another aspect of the invention, the introducer is rotated with the proximal end of the biopsy needle contained within the lumen. The biopsy needle is then readvanced to eject the proximal end of the biopsy needle from the lumen to obtain a second biopsy sample site from a location eccentric from the first biopsy sample site.

The invention also provides methods of making guide devices. According to the methods of this invention, a hollow cannula defining a lateral opening in communication with the lumen is provided, a hub is attached to an end of the cannula and the solid tip is secured to the cannula. In one aspect of the invention, the securing step includes inserting an end of the tip into the first end of the cannula, crimping the cannula onto the tip for temporary fixation and then welding the tip to the cannula.

In still another embodiment, systems are provided for diagnosing and treating a lesion inside a body. The systems include guide devices in combination with biopsy needles, localization wires, visualization wires, ablation means and pharmaceuticals. Advantageously, a lesion can be biopsied and treated through a single placement of the guide device. Multiple locations of a lesion can be biopsied and treated through a single device placement.

The invention also includes methods for delivering therapeutic items to a pathological site inside a patient's body. The methods include inserting an introducer guide of this invention into the patient near the site and manipulating the cannula to position the lateral opening adjacent the site. A pharmaceutical agent such as an ablation composition can then be advanced through the lumen of the cannula to the site.

Accordingly, it is an object of the invention to provide a surgical and pharmaceutical site access guide device which allows coaxial, cofocal and eccentric sampling and/or delivery to the site with a single device placement. One advantage of the present invention is that it compensates for placement errors without requiring multiple device placements. Another advantage of this invention is that it accommodates the need for obtaining multiple samples/deliveries around a lesion or target tissue without requiring multiple device placements.

Another object of the invention is to provide improved devices having safety features. The present invention provides means for protecting practitioners from inadvertent needle sticks. The designs of this invention also decrease the trauma to the patient.

Finally, it is an additional object of this invention to provide tools for percutaneous procedures which are cost effective to make and relatively easy to use. The present invention provides simpler, more efficient operation which may decrease surgical time and increase accuracy. This invention provides elegant constructs which are less likely to malfunction than the more complicated spring operated and/or multi-component devices found in the prior art.

These and other objects, advantages and features are accomplished according to the devices and methods of the following description of the preferred embodiment of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention provides surgical and pharmaceutical site access guide devices and methods for accessing locations within the body. This invention is advantageous anytime it is beneficial to change the direction or location of a device placement such as for biopsy, breast mass needle localization wire placement, ablation or radioactive seed placement. The present invention provides many benefits such as extremely precise tissue sampling and improved safety features. This invention compensates for sampling and placement errors and accommodates the need for obtaining multiple samples without multiple device placements by converting peri-target placement into successful placement without repositioning the device. Devices according to this invention also allow the practitioner to safely reach behind important vascular structures to obtain samples from target tissue or lesions. The invention also protects the tissue surrounding the lesion from unnecessary trauma. Furthermore, the present invention also provides features which protect the practitioner from inadvertent needle sticks.

This invention also answers the need for improved devices and methods for percutaneous treatments. In one aspect, the invention provides guide devices for locally treating a lesion within the body of a patient. The guide devices provide less traumatic and minimally invasive yet highly accurate placement of therapeutic agents at a lesion. In another embodiment, methods are provided for accessing, diagnosing and treating a lesion with a single guide placement. These methods significantly reduce trauma, risk and patient inconvenience.

Figure 1:
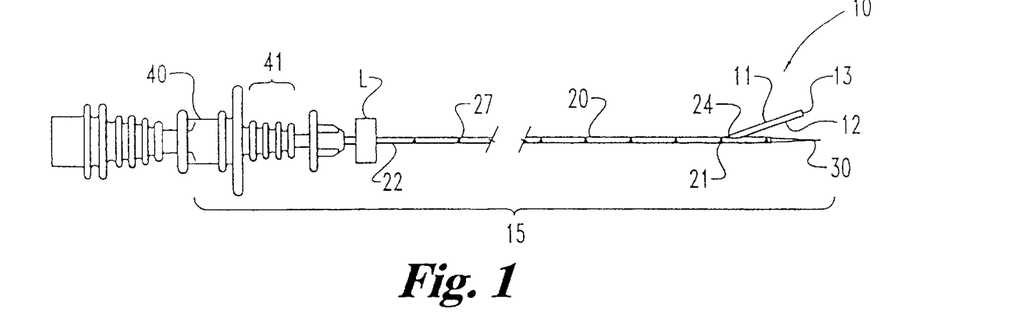
FIG. 1 is a side elevational view of a biopsy assembly according to this invention.

A biopsy device assembly 10 in accordance with one preferred embodiment of the present invention is depicted in FIG. 1. Generally, the biopsy assembly 10 includes a biopsy needle 11 and an introducer 15 which is more clearly shown in FIG. 2. The introducer 15 includes a cannula 20 having a first end 21 and a second end 22. The cannula 20 defines a lumen 25 which extends between the first end 21 and the second end 22 of the cannula 20 as shown more clearly in FIG. 3. A tip 30 which closes the lumen 25 is disposed at the first end 21 of the cannula 20. The cannula 20 defines an aperture 23 at the second end 22 of the cannula 20. The aperture 23 is in communication with the lumen 25 and is sized and configured to receive a biopsy needle 11 for passage into the lumen.

The cannula 20 also defines a lateral opening 24 which is in communication with the lumen 25. The lateral opening 24 is preferably adjacent the first end 21 of the cannula 20. The lateral opening 24 is sized and configured to allow exit of a biopsy needle from the cannula as it is advanced through the lumen 25.

The lateral opening 24 allows the practitioner to sample multiple areas within a sampling zone defined around the introducer 15. The introducer 15 can be rotated so that the lateral opening 24 will be exposed to different areas within the sampling zone, so that a biopsy needle 11 can be directed into these different areas. In this way, a single placement of the biopsy device, or introducer, provides cofocal and eccentric sampling as well as coaxial sampling. Typical biopsy needles allow coaxial sampling by varying the depth of the needle placement but require additional device placements for cofocal or eccentric sampling. This invention, on the other hand, allows the practitioner to return to the precise location within the target tissue with a second biopsy needle by leaving the introducer in place.

Figure 3:
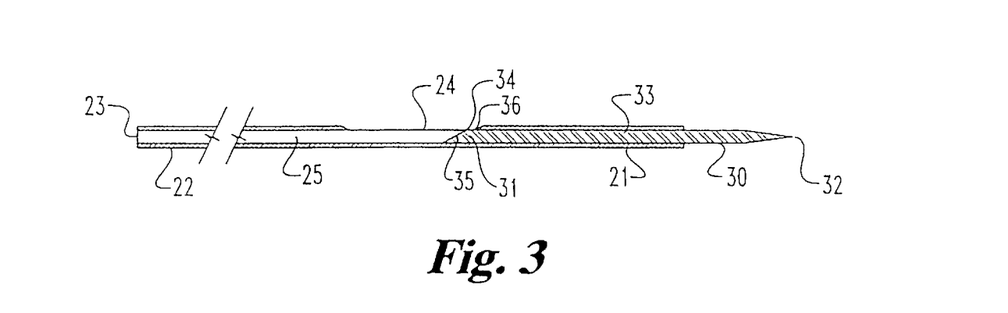
FIG. 3 is an enlarged side cross-sectional view of the needle introducer shown in FIG. 2.
Figure 4:
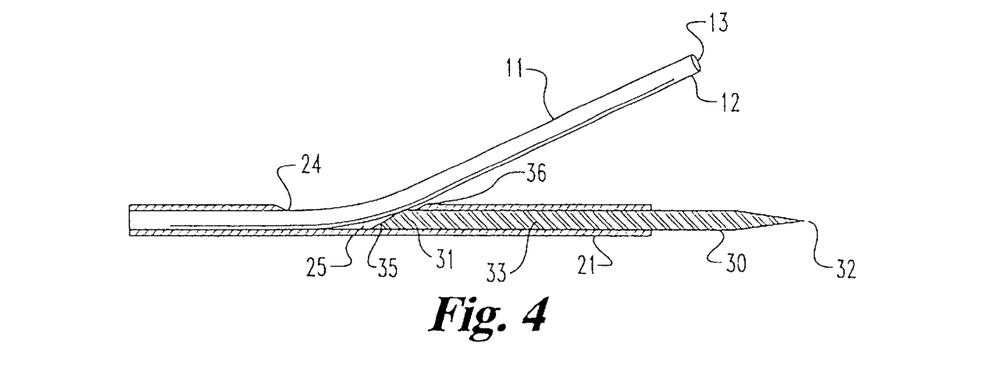
FIG. 4 is an enlarged side cross-sectional view of the biopsy assembly shown in FIG. 1.
Figure 5:
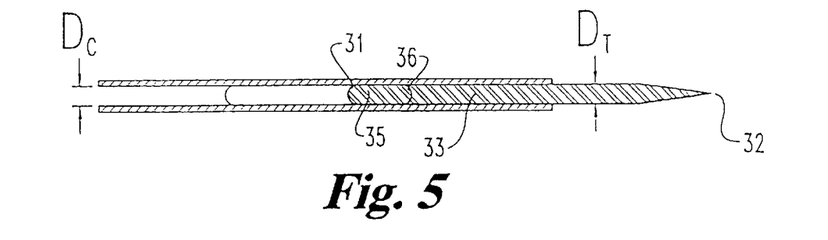
FIG. 5 is an enlarged top cross-sectional view of the proximal end of the needle introducer shown in FIG. 2.

As shown in FIGS. 3–5, the introducer 15 preferably includes a ramp 35 disposed within the cannula 20 at an end 36 of the lateral opening 24 adjacent the first end 21 of the cannula 20. The ramp 35 is inclined toward the lateral opening 24. In the operation of the biopsy assembly 10, a biopsy needle 11 will be deflected through the lateral opening 24 as it is advanced through the lumen 25 and exits the cannula 20. The ramp 35 provides controlled exit of the biopsy needle 11. The slope of the ramp may be altered to obtain a desired angle of deflection of the needle 11 as it exits the lateral opening 24.

In a preferred embodiment, the solid tip 30 is preferably a separate component which is secured to the first end 21 of the cannula 20 as shown in FIGS. 2–5. The anatomically distal end 31 of the tip 30 can be secured to the cannula 20 using any suitable means. The tip 30 includes a shaft 33 extending between the distal end 31 and the proximal end 32. The tip 30 also includes an anatomically proximal end 32 which is configured to pierce tissue. The proximal end 32 preferably extends beyond the first end 21 of the cannula 20. The solid tip 30 can be provided in any length which suits the particular application varying the length of the solid tip varies the distance from the proximal end 32 to the lateral opening 24 and from the proximal end 32 of the tip 30 to the proximal end 12 of the needle 11.

It is contemplated that the proximal end 32 has a configuration that is suited for the particular tissue to be sampled. For example, the tip may be beveled. In one embodiment, the tip has a trocar geometry. The multiple bevels of the trocar tip are useful in combination with a higher gage cannula for use in denser tissue. In one specific embodiment, a trocar tip is used with an 18 gage cannula. A single bevel is useful in combination with a thinner gage cannula for applications which require steering or for use in less dense tissue. For example, sampling lymph node tissue generally requires a smaller gage cannula, and consequently is better served by a single bevel tip.

Turning back to the distal end 31 of the tip 30, this end is preferably sloped to form the ramp 35. In a specific embodiment, as shown more clearly in FIG. 3, a portion 34 of the shaft 33 extends slightly into the lateral opening 24. This provides a smooth exit of the biopsy needle 11 through the lateral opening 24 and prevents catching of the needle 11 on the cannula 20 near edge of the lateral opening 24.

Preferably, the distal end 31 of the tip 30 has an outer diameter $D_t$ which is smaller than an inner diameter $D_c$ of the first end 21 of the cannula 20. The distal end 31 of the tip 30 is then at least partially disposed within the lumen 25 at the first end of the cannula 20. The tip 30 can be secured to the cannula 20 by an interference fit. Preferably, the cannula 20 is crimped onto the solid tip 30 to hold the tip in the desired position within the cannula while the tip is laser welded to the cannula. It is contemplated that the cannula 20 can also be secured to the tip 30 by any other suitable means including an adhesive.

Figure 2:
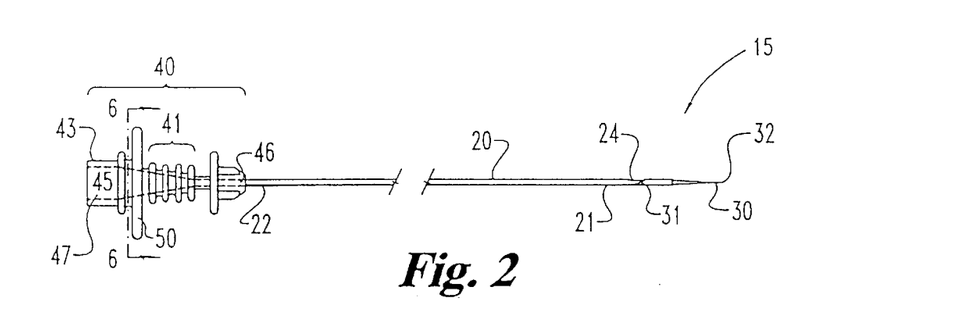
FIG. 2 is a side view of-the needle introducer shown in FIG. 1 with a partial longitudinal section of the proximal end of the introducer.
Figure 6:
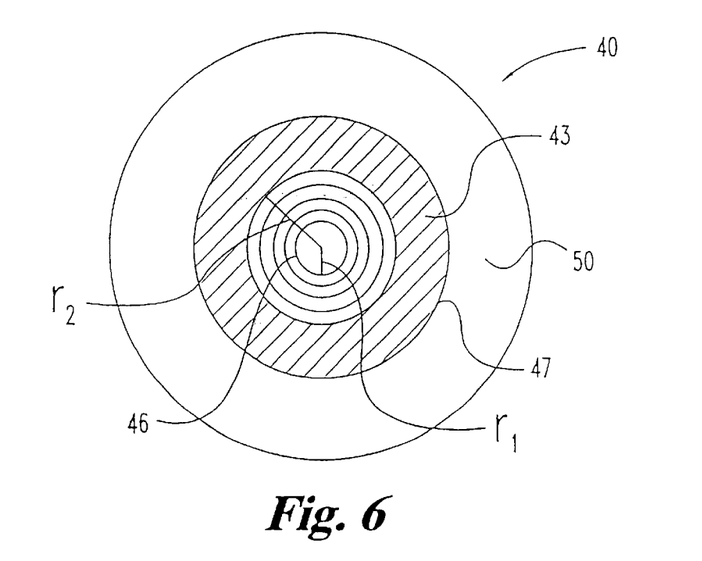
FIG. 6 is an end cross-sectional view of the introducer shown in FIG. 2 taken along lines 6—6.

In a preferred embodiment, the invention includes a hub 40 attached to the second end 22 of the cannula 20 as depicted in FIG. 2. Referring also to FIG. 6, hub 40 defines a channel 45 for delivering a biopsy needle to the cannula 20. The channel 45 includes a first end 46 and a second end 47. The first end 46 of the channel 45 surrounds the second end 22 of the cannula 20 and is in communication with the aperture 23. The channel 45 of the hub 40 is preferably funnel shaped as shown in FIGS. 2 and 6. The first end 46 of the channel 45 has an interior radius $R_i$ that is smaller than the interior radius $R_2$ of the second end 47 of the channel 45. The channel 45 tapers from the second end 47 of the channel 45 to the first end 46 of the channel 45 to guide a biopsy needle from the hub 40 to the lumen 25 of the cannula 20.

The hub 40 also preferably includes a fitting end 43 adjacent the second end of the channel. The fitting end 43 is configured for engagement with a stylet or a syringe. It is contemplated that the fitting end 43 will be of any suitable configuration including, but not limited to, a Luer® fitting.

Figure 7:
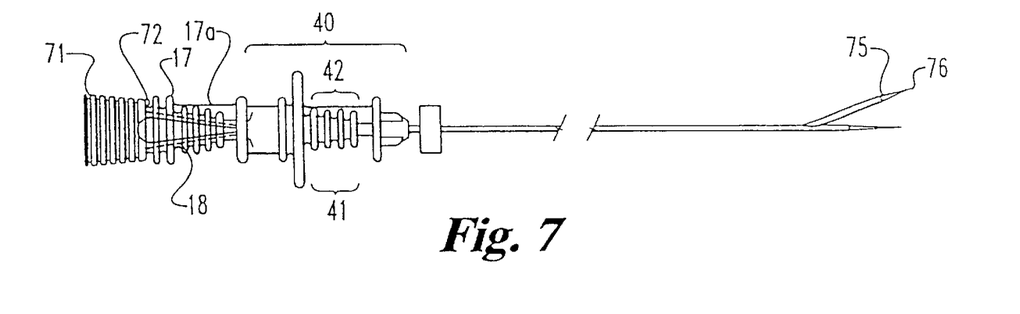
FIG. 7 is a side elevational view of the biopsy assembly shown in FIG. 1 with a biopsy needle stylet in place.

The hub 40 preferably includes a gripping portion 41 as shown in FIG. 2. The gripping portion 41 is configured to be held by the practitioner during insertion and positioning of the introducer 19. In one embodiment, the gripping portion 41 of the hub 40 includes a flattened portion 42 which provides the practitioner with a more stable grip on the hub 40 as depicted in FIG. 7. The flattened portion 42 also provides a tactile reference point for the location of the lateral opening 24. Preferably the flattened portion 42 is oriented on the same side of the cannula 20 as the lateral opening 24; however, any orientation is contemplated as long as it indicates the relative position of the lateral opening 24.

Referring again to FIG. 1, the cannula 20 of the introducer 19 preferably includes a plurality of depth markings 27 located in spaced relation along the cannula 20. These markings are preferably arranged in groups of five to give a ready visual indication of the depth of insertion of the cannula 20. Where the cannula 20 is composed of titanium, at least some of the depth markings 27 are preferably radiographic.

The present invention provides means for protecting the practitioner from health risks. In one preferred embodiment, the introducer 15 includes a flange 50 projecting from the hub 40 at a location anatomically distal from the gripping portion 41. The flange 50 is configured to prevent inadvertent needle sticks when the practitioner is holding the hub 40 during insertion of a biopsy needle into the introducer. This is particularly valuable when a biopsy needle is reinserted into the introducer. In light of the attention given to blood borne diseases in recent years, the need for such features is self evident. Any size or shape flange is contemplated which will protect the practitioner's fingers from needle sticks. Preferably, the flange is circular and extends from the hub at least 15 mm. Most preferably, the circular flange includes a flattened portion which prevents rolling of the device when it is placed on a flat surface. Alternatively, the flange can be hexagonal or octagonal providing many flat sides.

Figure 8:
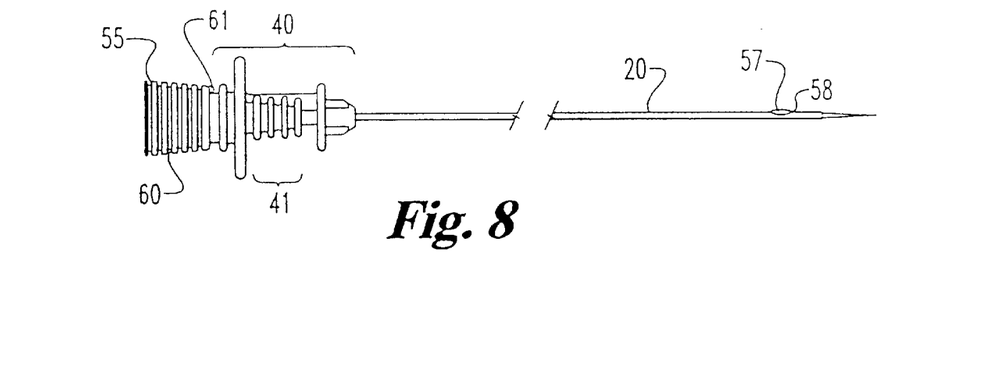
FIG. 8 is a side elevational view of the introducer of FIG. 2 having an introducer stylet in place.
Figure 9:
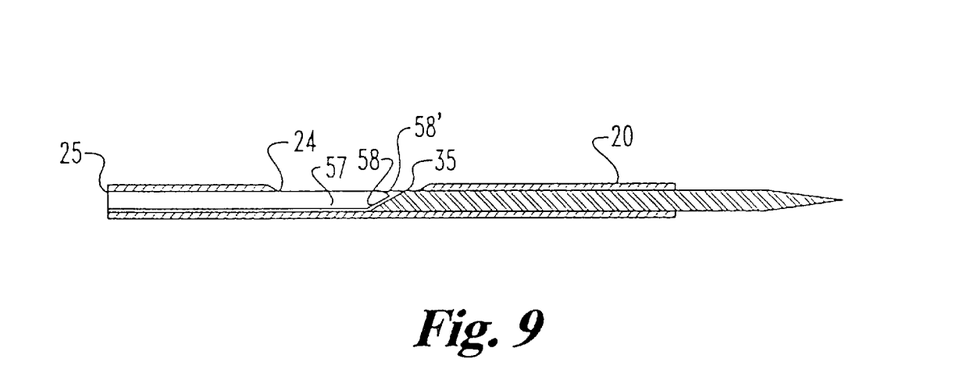
FIG. 9 is an enlarged side cross-sectional view of the proximal end of the needle introducer shown in FIG. 2 with an introducer stylet in place.

Referring now to FIGS. 8 and 9, the invention contemplates an introducer stylet 55 which includes a shaft 57 and a grip 60. The shaft 57 is sized to be received within the lumen 25. Preferably, the introducer stylet 55 has a length sufficient to block the lateral opening 24 when the introducer stylet 55 is received within the lumen 25. Most preferably, the introducer stylet 55 has an angled end 58 which is configured to mate with the ramp 35 when the introducer stylet 55 is received within the cannula 20. Blocking the lateral opening 24 is important to reduce trauma to the surrounding tissue and preserve the integrity of the sample by preventing tissue from entering the lateral opening 24 as the introducer is guided into the patient. Trauma can be further reduced by providing an atraumatic feature, such as bevel 58', to the end 58 of the stylet 55. The introducer stylet 55 also provides stiffness to the introducer cannula 20 to facilitate insertion.

The biopsy assembly 10 shown in FIG. 1 includes a hollow biopsy needle 11 having an anatomically proximal end 12 and a distal end (not shown). The biopsy needle 11 is sized and configured to be movably, rotatably and coaxially received within the lumen 25. The proximal end 12 of the biopsy needle 11 is sized and configured to exit from the lumen 25 through the lateral opening 24 as shown in FIG. 4. The biopsy needle 11 preferably includes an edge 13 which is configured to pierce tissue to obtain a biopsy sample when the biopsy needle 11 is advanced into tissue.

Figure 10:
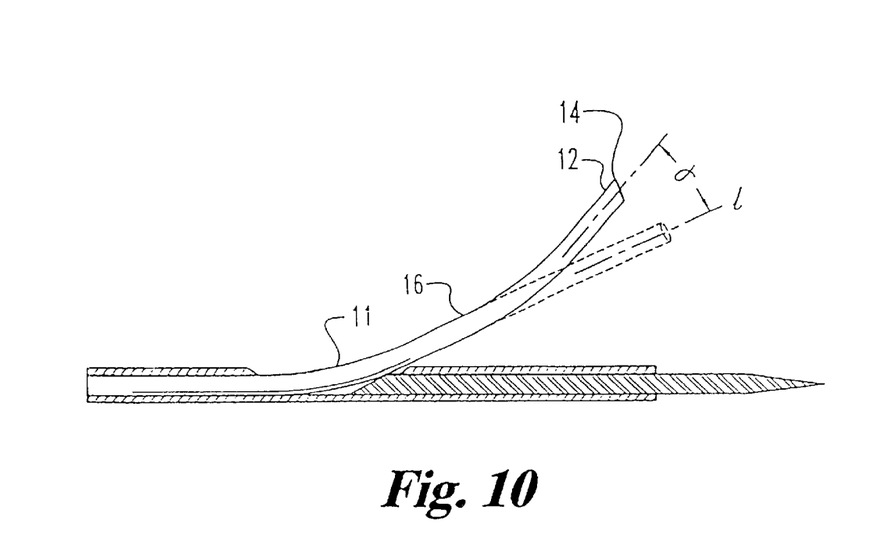
FIG. 10 is an enlarged side cross-sectional view of the proximal end of a biopsy assembly incorporating a biopsy needle having a bend.

Any suitable biopsy needle is contemplated. Standard hollow biopsy needles are preferred, such as the Mengehni type. The proximal end 12 of biopsy needle 11 includes an edge or tip that may be of any suitable configuration. As shown in FIG. 4 the edge 14 may be blunt. As shown in FIG. 10, the edge 14 may be beveled. The biopsy needle may further include a needle hub which may include a channel 18 which is preferably funnel shaped as described above for the introducer hub 40. The biopsy needle hub 19 may also include a flattened portion 19A which provides a gripping and reference function as described above.

In one embodiment the biopsy needle 11 includes a bend 16 adjacent the proximal end 12 of the needle 11 as shown in FIG. 10. The bend 16 deflects the proximal end 12 of the needle 11 at an angle $\alpha$ away from a longitudinal axis 11 of the needle 11 when the bend 17 extends outside the cannula 20. The bend 16 increases the diameter of the sampling zone of the tissue. Multiple samples in a single plane can also be obtained by providing needles having bends of varying angles and curves. The angle $\alpha$ is preferably between 5° and 30°. The most preferred angle $\alpha$ being about 15°. Where the needle 11 is bent, the ramp 35 may include a concavely curved surface to facilitate smooth exit of the needle 11 through the lateral opening 24.

As shown in FIG. 7, the invention also contemplates a biopsy needle stylet 70. The biopsy stylet 70 facilitates guiding the biopsy needle 11 through the lateral opening 24. The biopsy needle stylet 70 includes a handle 71 and a shaft 75. The handle 71 may include a locking nub 72 which mates with a notch (not shown) on the biopsy needle hub 17 for locking the biopsy stylet into place. The shaft 75 of the biopsy stylet 70 is sized and configured to be received within the biopsy needle 11. Preferably, the biopsy needle stylet 70 has a penetrating point 76 that extends away from the proximal end of the biopsy needle 11 when the biopsy needle stylet 70 is inserted into the biopsy needle 11. The penetrating point 76 aids collection of the sample by piercing the tissue before the tissue is collected within the needle 11. Any suitably shaped penetrating point is contemplated. For example, penetrating point 76 may be rounded or may have a trocar geometry.

Methods of obtaining a biopsy sample are also contemplated by the present invention. Preferably, the methods of this invention are practiced in combination with an imaging study to determine the appropriate needle path to the biopsy sample site. The methods include providing a biopsy introducer of the present invention and inserting the biopsy introducer into the patient at the biopsy sample site using standard surgical procedures. Preferably, the methods of this invention also include inserting an introducer assembly which includes an introducer stylet inserted into the cannula. The introducer stylet is sized to be received within the lumen and preferably has a length such that it will block the lateral opening when the introducer stylet is received within the lumen to prevent tissue from entering the lateral opening when the cannula is introduced into the patient. The introducer stylet also provides stiffness to the introducer cannula to facilitate inserting the introducer into tissue. Once the introducer assembly is inserted, the practitioner removes the introducer stylet.

Once the introducer is in place, the invention includes inserting a biopsy needle having an anatomically proximal end and a distal end through the aperture and into the lumen of the introducer, advancing the biopsy needle through the lumen so that the proximal end of the biopsy needle projects through the lateral opening at an angle relative to the introducer and into a first biopsy sample site to obtain a first biopsy sample, and then withdrawing the proximal end of the biopsy needle from the first biopsy sample site and into the lumen of the introducer. As is well known in the art, a locking member L such as the one shown in FIG. 1 can be used to control the depth of the introducer.

The biopsy needle may be provided with a biopsy needle stylet inserted into the lumen of the hollow biopsy needle. The practitioner will remove the biopsy needle stylet after the biopsy needle has been inserted into the lumen of the introducer. The biopsy needle stylet provides stiffness to the hollow biopsy needle which facilitates guiding the needle through the lateral opening. Preferably, the stylet includes a penetrating tip which pierces the subject tissue as the needle-stylet assembly is advanced through the lumen of the introducer and into the tissue.

After the stylet is removed, a sample is collected. The sample is preferably collected by applying suction to the biopsy needle to draw a first biopsy sample into the biopsy needle through its proximal end. Suction may be applied in any suitable manner. Preferably a syringe will be attached to the Luer fitting on the hub of the introducer to draw a vacuum Most preferably, the collecting step will also include reciprocating the biopsy needle within the lumen while applying suction so that the needle edge can help excise the tissue.

This invention contemplates that multiple samples which are cofocal, coaxial and eccentric to the original biopsy sample can be taken in this manner with only a single placement of the biopsy device. The tissue that is available to be sampled can be increased by rotating the introducer to change the exposure of the lateral opening or by altering the shape of the biopsy needle.

In one embodiment of the invention, the methods include removing the biopsy needle from the introducer after withdrawing the biopsy needle from the biopsy site, clearing the sample from the biopsy needle, rotating the introducer, reinserting the biopsy needle through the aperture and into the lumen after clearing the sample, further advancing the biopsy device to eject the proximal end of the biopsy needle from the lumen through the lateral opening at the same angle relative to the introducer to obtain a second biopsy sample from a location eccentric from the first biopsy sample, and withdrawing the proximal end of the biopsy needle from the biopsy sample site into the lumen of the introducer. Although the biopsy needle is removed from the sample site, the introducer is left in place. Therefore, the practitioner is able to insert the needle in a precise location relative to the initial sample site.

Alternatively, the methods may include rotating the introducer with the proximal end of the biopsy needle contained within the lumen and then further advancing the biopsy device to eject the proximal end of the biopsy needle from the lumen through the lateral opening. A second biopsy sample may be obtained from a location eccentric from the first biopsy sample. Additional samples may be taken which are cofocal, coaxial and eccentric from the original sample can be taken without clearing the sample from the needle.

The methods of this invention also contemplate that the sample site accessible to the single biopsy device placement can be broadened by adjusting the angle by which the biopsy needle is deflected from the cannula. This may be accomplished by either providing a second biopsy needle having a bend adjacent an anatomically proximal end of the needle, the bend deflecting the proximal end of the second needle at an angle away from a longitudinal axis of the second needle or by bending the first biopsy needle in a similar manner. The bent needle is similarly inserted through the aperture and into the lumen and advanced so that the proximal end projects through the lateral opening at a different angle relative to the introducer to obtain a second biopsy sample. For example, the second biopsy sample site may be located in a plane defined by the first biopsy sample site and the introducer or may be eccentric to the first site. The invention contemplates rotating the introducer and bending the needle so that the desired tissue location may be reached.

Figure 11:
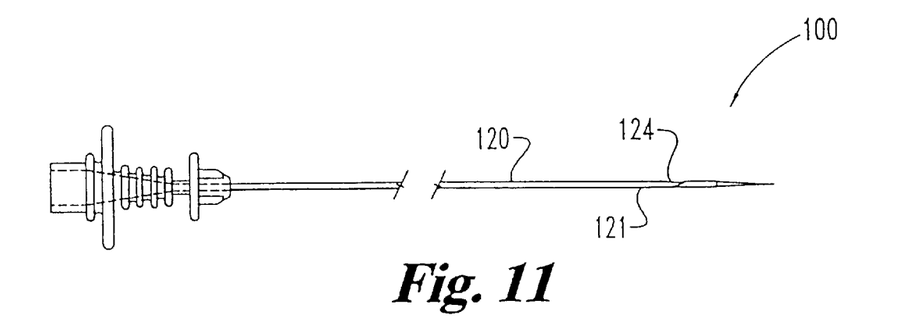
FIG. 11 is a side view of an introducer guide of this invention.

This invention also provides devices and methods for treating lesions located within a patient's body. An introducer-guide 100 is shown in FIG. 11. The guide 100 is similar to the introducer 15 shown in FIG. 2. In fact, in some methods it is preferable that the same introducer be used first for diagnosis and then for treatment of a lesion in a single procedure. The guide 100 includes a cannula 120 having a first end 121 and a second end 122. The cannula 120 defines a lumen 125 which extends between the first end 121 and the second end 122 of the cannula 120 as shown more clearly in FIG. 12. A tip 130 which closes the lumen 125 is disposed at the first end 121 of the cannula 120. The cannula 120 defines an aperture 123 at the second end 122 of the cannula 120. The aperture 123 is in communication with the lumen 125 and is sized and configured to receive a therapeutic or diagnostic item for passage into the lumen 125. It is contemplated that the item could be mechanical, chemical or photo (laser) ablation means, a biopsy needle, a breast mass localization wire, a radiopharmaceutical composition, such as radioactive seeds, a visualization agent, such as a contrast dye and the like.

The cannula 120 also defines a lateral opening 124 which is in communication with the lumen 125. The lateral opening 124 is preferably adjacent the first end 121 of the cannula 120. The lateral opening 124 is sized and configured to allow exit of the item from the cannula as it is advanced through the lumen 125. As described above for the biopsy system, the introducer 100 preferably includes a ramp 135 disposed within the cannula 120 at an end 136 of the lateral opening 124 adjacent the first end 121 of the cannula 120. The ramp 135 is inclined toward the lateral opening 124 and provides controlled exit of items exiting the lateral opening 124.

Figure 12:
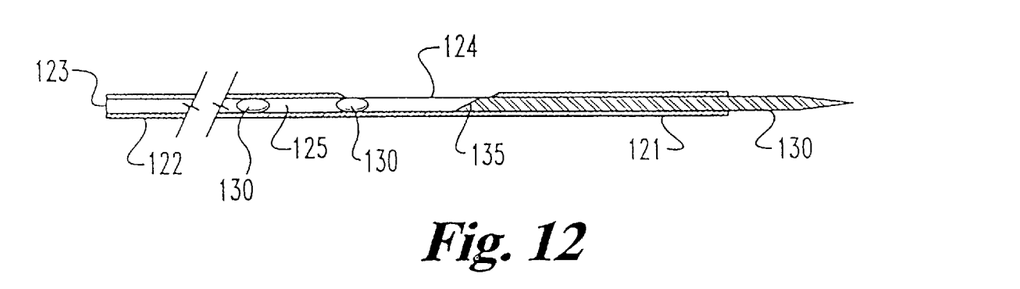
FIG. 12 is an enlarged side longitudinal view of the introducer shown in FIG. 11.

In the embodiment shown in FIGS. 11 and 12, the lumen is packed with radioactive seeds 130. The seeds 130 can be implanted into an organ, such as the prostate, using conventional procedures which are greatly aided by the use of the guide 100. One procedure is described in Grimm, 1994. Under ultrasound visualization, the guide 100 is inserted into the patient. In one embodiment, the guide 100 is inserted into the prostate and the seeds 130 are ejected. The guide 100 can then be rotated to direct the lateral opening 124 in another direction.

Figure 13:
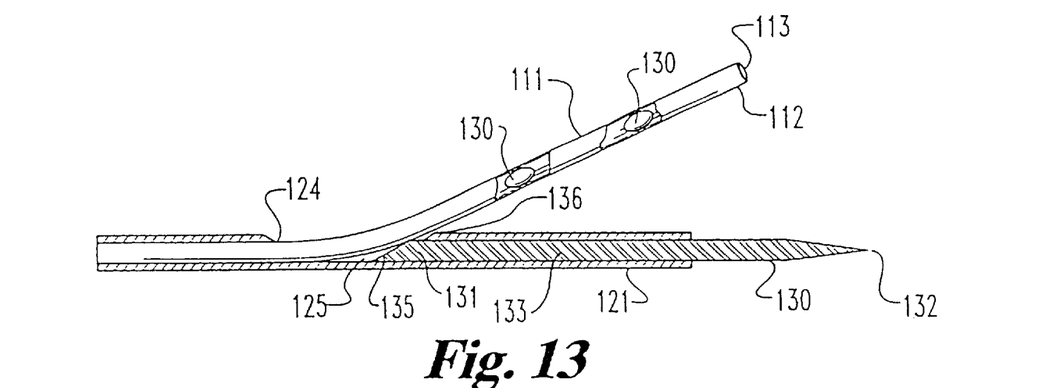
FIG. 13 is an enlarged longitudinal view of the introducer of FIG. 11 loaded with pharmaceutical pellets.

In a preferred embodiment, the guide 100 is inserted near the prostate. An insertion needle 111 is packed with the seeds 130 and then inserted through the lumen 125 of the guide 100 as shown in FIG. 13. As described above for the biopsy procedure, the path of the insertion needle 111 can be adjusted as required to correct a miss-hit or for multiple seed 130 placements. Once the guide 100 is properly positioned, it serves as a reference point for multiple insertion needle 111 placements.

Figure 14:
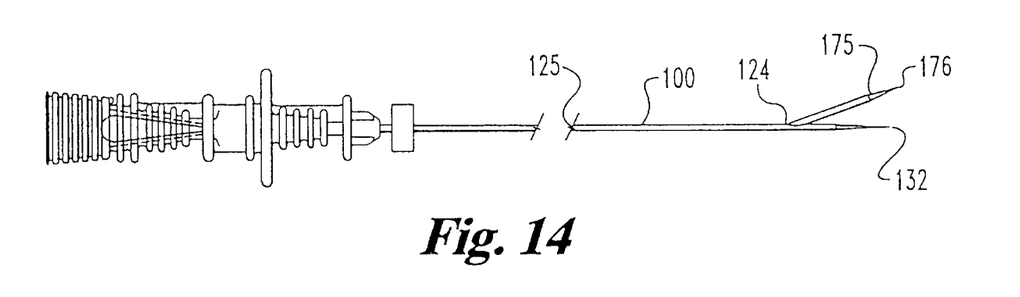
FIG. 14 is a side elevational view of the introducer of FIG. 11 loaded with a mechanical ablation needle.

In some embodiments, the therapeutic item is an ablation means for ablating a lesion such as a tumor. In one embodiment depicted in FIG. 14, an ablation needle 175 having a cutting edge 176 is provided. This device can be used for mechanical ablation of small benign lesions such as arteriovenous malformations. In operation of the device, the guide 100 is inserted into the patient with the proximal end 132 as close to the lesion as possible. The ablation needle 175 is inserted through the lumen 125 and out through the lateral opening 124 to the lesion. Using the guide 100, innumerable needle passes can be made through the entire lesion.

Figure 15:
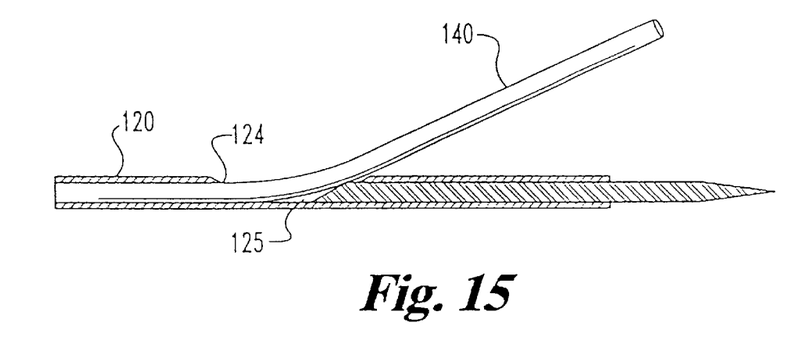
FIG. 15 is a side elevational view of the introducer of FIG. 11 loaded with a chemical ablation needle.

In another embodiment, the ablation means is a chemical composition such as ethanol or cyanoacrylate. Fine-needle alcohol ablation is described in Karstrup 1990. (See also, Karstrup, et al. Br. J Radiol 60: 667–670, 1987 and Solbiati, et al. Radiology 155: 607–610, 1985). The guide 100 of this invention allows precise fine needle placement into multiple locations with a single guide 100 placement. The cannula 120 of the guide 100 can be adjusted coaxially or rotated to change the direction of the lateral opening 124. Referring now to FIG. 15, a fine needle 140 is preferably inserted through the lumen 125 and opening 124 to provide small controlled doses of ablation agent to multiple locations in the lesion. This invention addresses the need for highly precise placement of the ablation agent. As with the biopsy needle placements described above, the introducers of this invention allow extremely precise delivery without requiring extremely precise introducer placement.

The devices, systems and methods are particularly beneficial when used in combination with imaging technology, preferably ultrasonography, CT or MR. Precise, yet minimally invasive, diagnostic and therapeutic procedures are possible using this invention under imaging guidance. The path of a needle or other object can be guided to an exact location. The use of image guided access for biopsy and therapy is discussed in Dietrich, et al., Suppl. to Diag Imaging, November 1996 and Karstrup et al., Acta Radiological 29:213–216, 1988.

Although a few embodiments are described here, this invention is not intended to be limited to these systems and procedures. The introducer-guides of this invention can be used for placement for any suitable therapeutic or diagnostic item, particularly where a change in direction from a fixed initial position is desired. For example, this invention may also be employed in galactography, or mammary duct contrast examination. (Diner, AJR 137:853–856, 1981; Tabar et al, Radiology 149:31–38, 1983; Threatt and Appelman, Radiology 108:71–76, 1973.) The present invention is useful is procedures such as galactography where the most difficult step is proper insertion and positioning of a needle or other item.

This invention also provides methods of making a guide device. The methods include: attaching a hub defining a channel to a hollow cannula and securing an anatomically distal end of a solid tip to the first end of the cannula. The hub is engaged to the cannula by conventional techniques such as insert molding. Preferably, the distal end of the tip has an outer diameter smaller than an inner diameter of the first end of the cannula and the securing includes inserting the distal end of said tip into the first end of the cannula. Preferably, the cannula has a very thin wall. In one embodiment, the securing includes employing a mechanical or interference fit, such as crimping the cannula onto the tip. The securing also preferably includes welding. Most preferably, the methods include laser welding or brazing the tip and the cannula after the cannula has been crimped into place on the tip. In a preferred embodiment, the cannula is crimped onto the tip so that the ramp formed by the tip is located to ensure that a biopsy needle advancing through the lumen does not catch on the portion of the cannula forming the lateral opening. Any methods which provide a smooth transition between the tip and the cannula are contemplated. A smooth transition reduces trauma to tissue during insertion of the device. Any other suitable methods of securing the tip to the cannula are contemplated including applying an adhesive.

The devices of the present invention may be provided in any suitable size and in any suitable material. For example, in one embodiment, the components are made from 300 series stainless steel. Alternatively, some of the components may be composed of titanium or Inconel. The size of the components are dictated by the type and location of the tissue to be sampled.

The present invention includes devices and methods that provide extremely precise sampling and/or delivery without requiring extremely precise device placements. The invention compensates for peri-site placement and accommodates the need for obtaining multiple placements around a lesion. The invention also provides safeguards for the practitioner and the patient.

All publications cited herein are hereby incorporated by reference in their entirety, as if each were individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A system for diagnosing and treating a lesion inside a patient, comprising:
    an introducer having
        a cannula having a first end and a second end and defining a lumen therebetween opening at a first aperture at said second end,
        said cannula defining a lateral opening in communication with the lumen adjacent said first end, and
        a solid tip having an anatomical distal end secured to the first end of said cannula and a proximal end, said distal end sloped to form a ramp adjacent and inclined toward said lateral opening, wherein said proximal end of said solid tip is configured to pierce tissue; and
    an item disposed within said lumen for transport through said lateral opening to the lesion.

2. The system of claim 1 wherein said item is a diagnostic item.

3. The system of claim 1 wherein said item is a therapeutic item.

4. The system of claim 1 further comprising a plurality of depth markings located in spaced relation on said cannula.

5. The system of claim 4 wherein said markings are radiographic.

6. The system of claim 1 further comprising a hub having a distal end and a proximal end, said distal end of said hub attached to said second end of said cannula, said hub including a gripping portion for holding, inserting and positioning said introducer, said hub defining a channel for receiving said item and delivering said item to said lumen of said cannula.

7. The system of claim 6 further comprising a flange projecting from said hub at a location anatomically distal from said gripping portion.

8. A system for diagnosing and treating a lesion inside a patient, comprising:
    an introducer having
        a cannula having a first end and a second end and defining a lumen therebetween opening at a first aperture at said second end, said cannula defining a lateral opening in communication with the lumen adjacent said first end;
        a ramp disposed within said lumen adjacent and inclined toward said lateral opening;
        a tip having an anatomical distal end secured to the first end of said cannula and a proximal end configured to pierce tissue; and
        an item disposed within said lumen for transport through said lateral opening to the lesion.

9. The system of claim 8 wherein said item is a diagnostic item.

10. The system of claim 8 wherein said item is a therapeutic item.

11. The system of claim 8 further comprising a plurality of depth markings located in spaced relation on said cannula.

12. The system of claim 11 wherein said markings are radiographic.

13. Then system of claim 8 further comprising a hub having a distal end and a proximal end, said distal end of said hub attached to said second end of said cannula, said hub including a gripping portion for holding, inserting and positioning said introducer, said hub defining a channel for receiving said item and delivering said item to said lumen of said cannula.

14. The system of claim 13 further comprising a flange projecting from said hub at a location anatomically distal from said gripping portion.

* * * * *